(12) United States Patent
Morimoto et al.

(10) Patent No.: US 10,228,327 B2
(45) Date of Patent: Mar. 12, 2019

(54) DATA PROCESSING APPARATUS, OPTICAL DETECTION SYSTEM, DATA PROCESSING METHOD, AND DATA PROCESSING PROGRAM

(71) Applicant: Sony Corporation, Tokyo (JP)

(72) Inventors: Naoki Morimoto, Tokyo (JP); Shinichi Kai, Tokyo (JP)

(73) Assignee: Sony Corporation, Tokyo (JP)

( * ) Notice: Subject to any disclaimer, the term of this patent is extended or adjusted under 35 U.S.C. 154(b) by 752 days.

(21) Appl. No.: 14/778,120

(22) PCT Filed: Feb. 19, 2014

(86) PCT No.: PCT/JP2014/053889
§ 371 (c)(1),
(2) Date: Sep. 18, 2015

(87) PCT Pub. No.: WO2014/156379
PCT Pub. Date: Oct. 2, 2014

(65) Prior Publication Data
US 2016/0282268 A1    Sep. 29, 2016

(30) Foreign Application Priority Data
Mar. 29, 2013    (JP) .................................. 2013-074925

(51) Int. Cl.
*G01J 3/00*    (2006.01)
*G01N 21/64*    (2006.01)
(Continued)

(52) U.S. Cl.
CPC ......... *G01N 21/6428* (2013.01); *G01N 21/01* (2013.01); *G01N 21/27* (2013.01);
(Continued)

(58) Field of Classification Search
CPC .... G01N 21/6428; G01N 21/01; G01N 21/27; G01N 21/6452; G01N 21/552; G01N 21/31; G01J 3/02; G01J 3/42
See application file for complete search history.

(56) References Cited

U.S. PATENT DOCUMENTS 6,108,023 A    8/2000  Seino
2004/0234114 A1  11/2004  Amakawa et al.
(Continued)

FOREIGN PATENT DOCUMENTS

CN    1573316 A    2/2005
CN    102419367 A    4/2012
(Continued)

OTHER PUBLICATIONS

Chinese Office Action dated Nov. 16, 2017 in connection with Chinese Application No. 201480017565.9 and English translation thereof.

*Primary Examiner* — Abdullahi Nur
(74) *Attorney, Agent, or Firm* — Wolf, Greenfield & Sacks, P.C.

(57) ABSTRACT

There is provided a data processing apparatus including: a data determination portion that specifies, in each of first and second light intensity distribution data, an analysis range corresponding to a storage area for storing a detection target, the first and second light intensity distribution data being acquired on the basis of light emitted from first and light sources to a detection area; and a mode selection portion that selects an operation mode of the data determination portion. The mode selection portion selects one of a first mode in which the data determination portion specifies the analysis range in each of the first light intensity distribution data and the second light intensity distribution data, and a second mode in which the data determination portion specifies the analysis range in the second light intensity distribution data (Continued)

on the basis of information on the analysis range of the first light intensity distribution data.

19 Claims, 15 Drawing Sheets

(51) Int. Cl.
*G01N 21/01* (2006.01)
*G01N 21/27* (2006.01)
*G01N 21/17* (2006.01)

(52) U.S. Cl.
CPC ....... *G01N 21/6452* (2013.01); *G01N 21/274* (2013.01); *G01N 2021/0175* (2013.01); *G01N 2021/178* (2013.01); *G01N 2021/1753* (2013.01); *G01N 2021/1789* (2013.01); *G01N 2021/6419* (2013.01); *G01N 2021/6439* (2013.01); *G01N 2021/6441* (2013.01); *G01N 2201/0446* (2013.01); *G01N 2201/0453* (2013.01); *G01N 2201/0484* (2013.01)

(56) References Cited

U.S. PATENT DOCUMENTS

| | | |
|---|---|---|
| 2005/0046849 A1 | 3/2005 | Cromwell et al. |
| 2007/0035819 A1 | 2/2007 | Bahatt et al. |
| 2007/0248490 A1 | 10/2007 | Matsuo et al. |
| 2011/0131021 A1 | 6/2011 | Xu et al. |
| 2012/0019165 A1* | 1/2012 | Igaki .................. G08C 17/02 |
| | | 315/294 |

FOREIGN PATENT DOCUMENTS

| | | |
|---|---|---|
| JP | 2001-091518 A | 4/2001 |
| JP | 2001-228088 A | 8/2001 |
| JP | 2006-284596 A | 10/2006 |
| JP | 2007-263912 A | 10/2007 |
| JP | 2009-053029 A | 3/2009 |
| JP | 2009-180606 A | 8/2009 |
| JP | 2011-522264 A | 7/2011 |

* cited by examiner

FIG. 8
A
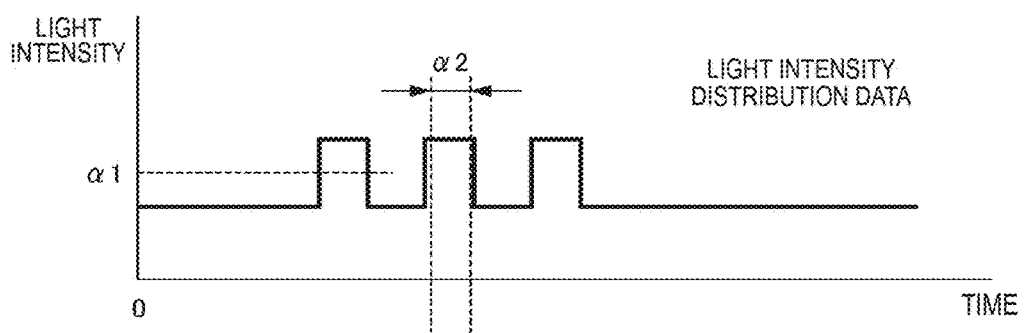
B
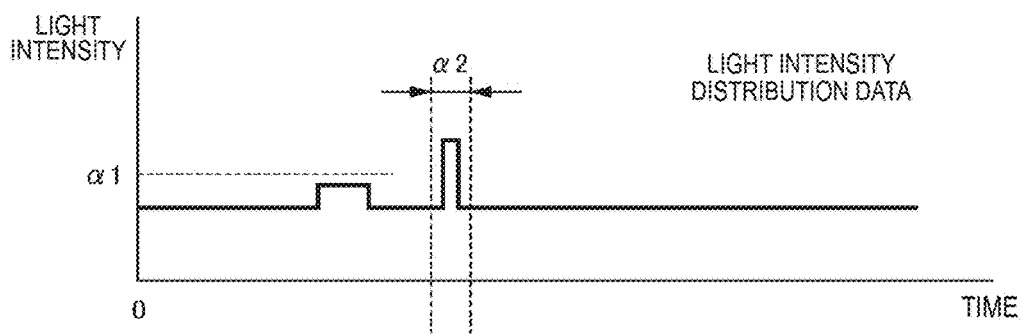

FIG. 9
A
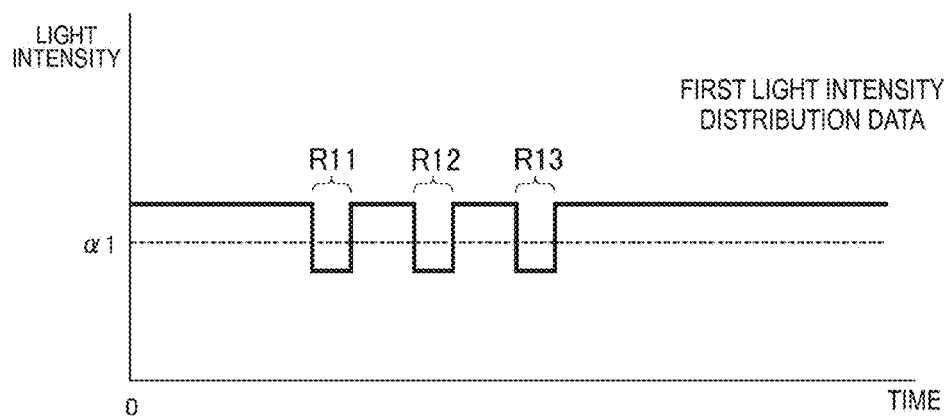
B
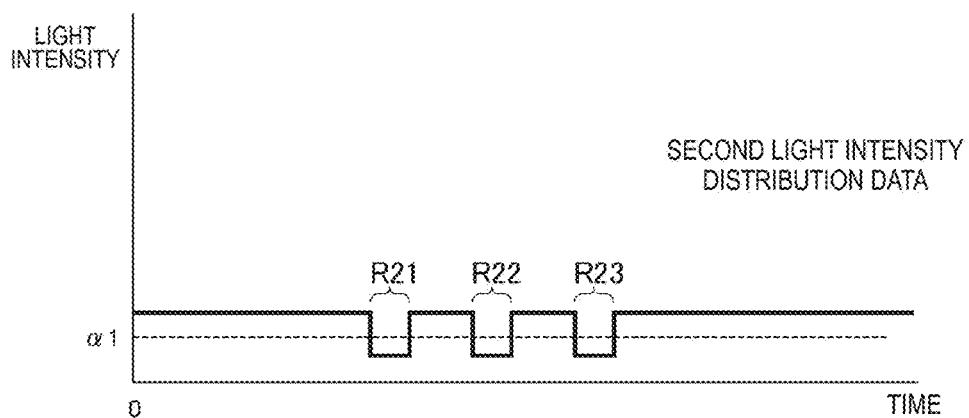

FIG. 11
A
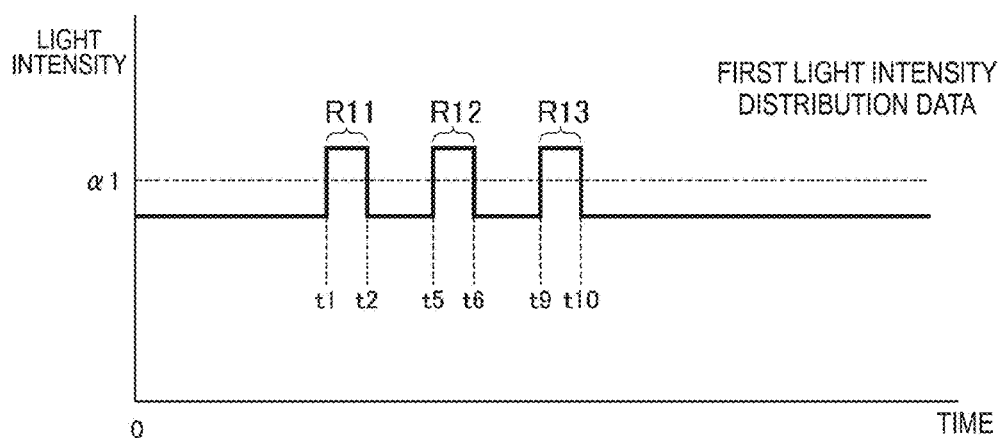
B
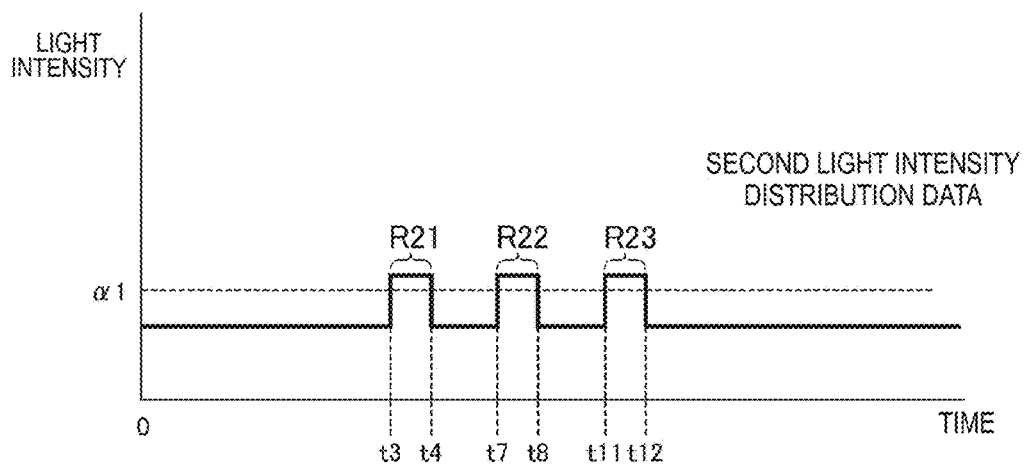

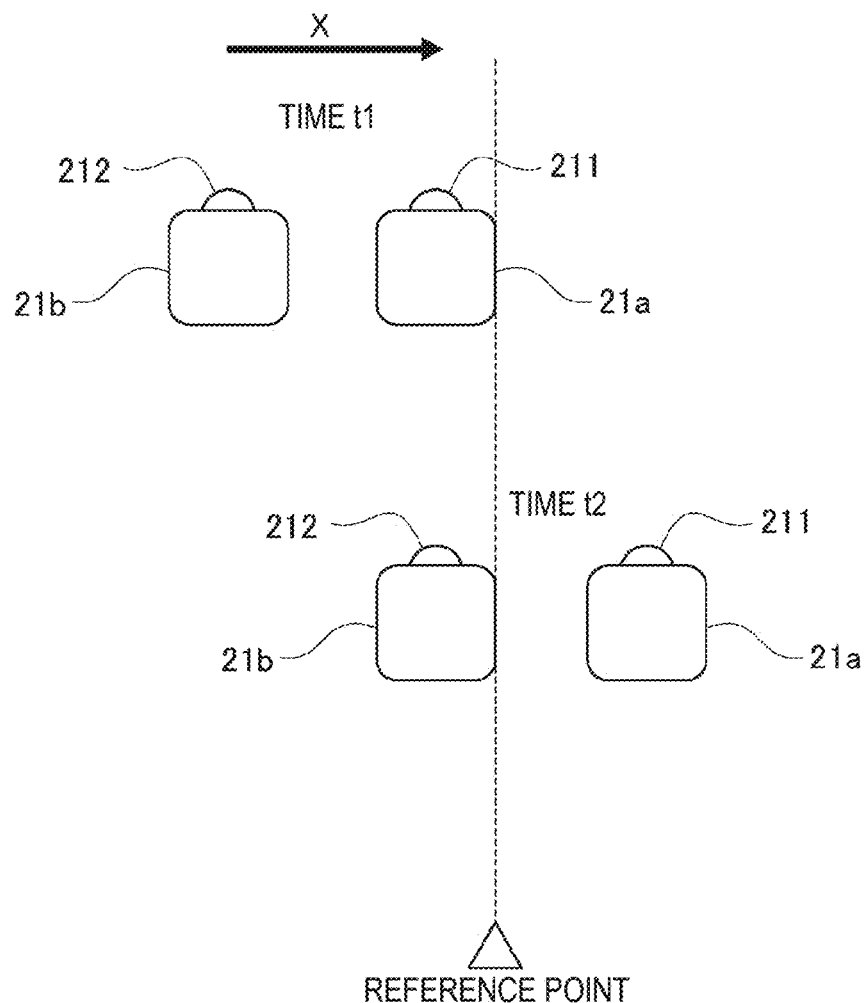

DATA PROCESSING APPARATUS, OPTICAL DETECTION SYSTEM, DATA PROCESSING METHOD, AND DATA PROCESSING PROGRAM

CROSS-REFERENCE TO RELATED APPLICATIONS

This application is a National Stage of International Application No. PCT/JP2014/053889, filed in the Japanese Patent Office as a Receiving office on Feb. 19, 2014, which claims priority to Japanese Patent Application Number 2013-074925, filed in the Japanese Patent Office on Mar. 29, 2013, each of which is hereby incorporated by reference in its entirety.

TECHNICAL FIELD

The present technology relates to a data processing apparatus, an optical detection system, a data processing method, and a data processing program. More specifically, the present technology relates to a technique to specify, in optical strength distribution data, an analysis range corresponding to a storage area that stores a detection target.

BACKGROUND ART

An apparatus that optically detects a detection target emits light from a light source of the apparatus to an area where the detection target is stored and detects light that is transmitted through the storage area or is emitted from the detection target, whereby the detection target is detected. To detect a plurality of detection targets contained in a sample at one time using the aforementioned optical detection apparatus, a plurality of lights with different wavelengths that are adopted to the optical properties of the detection targets are eventually used.

When an optical detection apparatus is used, a sample containing a detection target is often stored in a container suitable for optical detection. For example, microplates, microchips, and like containers that are formed with a plurality of holes called wells have been used since the past as containers storing a sample. When a container is provided with a plurality of areas storing a sample, as in the case of microplates and microchips, light needs to be irradiated from a light source to all areas in order to optically detect the detection target.

To irradiate light onto a plurality of areas in a single operation, for example, a plurality of optical systems, such as light sources, may be disposed on an optical detection apparatus. An optical detection apparatus may be configured such that an optical system, such as a light source, or an area storing a sample moves and the position of the area changes relative to the position of the optical system. As the relative position between the optical system and the area changes, a light source or the like can irradiate light onto a plurality of areas so that the light travels from one area to another in a consecutive order.

For example, Patent Literature 1 discloses "an optical biological sample scanning apparatus that scans light through sample chip with sequence of plural biological samples and specify biological sample labeled with fluorescent substance". In the optical biological sample scanning apparatus, a sample chip with a sequence of biological samples is set to a rotating table, whereby the sample chip, which rotates during straight movement of the sample chip, is spirally scanned by light and a biological sample attached with a fluorescent substance can be detected.

CITATION LIST

Patent Literature

Patent Literature 1 JP 2001-228088A

SUMMARY OF INVENTION

Technical Problem

The apparatus of Patent Literature 1 can irradiate light onto a plurality of areas in a consecutive order and detect a detection target in a sample stored in the plurality of areas. Measurement data, such as a series of light intensity data, can be acquired by the aforementioned continuous light detection. Such data needs to be divided into data derived from the detection target and noise data. Accordingly, it is required to specify, in a series of light intensity data, analysis ranges corresponding to the areas storing a sample. The reason is that by specifying the analysis ranges, light detected outside the boundary of the analysis ranges is prevented from being erroneously determined as a signal derived from the detection target during data analysis.

In view of the foregoing, the present technology is mainly directed to providing, inter alia, a data processing apparatus that can accurately specify, in a series of light intensity data, a range corresponding to an area storing a sample.

Solution to Problem

According to the present technology, there is provided a data processing apparatus including: a data determination portion that specifies, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area; and a mode selection portion that selects an operation mode of the data determination portion. The mode selection portion selects one of a first mode in which the data determination portion specifies the analysis range in each of the first light intensity distribution data and the second light intensity distribution data, and a second mode in which the data determination portion specifies the analysis range in the second light intensity distribution data on the basis of information on the analysis range of the first light intensity distribution data.

The first light intensity distribution data and the second light intensity distribution data may be acquired on the basis of light emitted from the first light source whose relative position to a position of the storage area changes, and on the basis of light emitted from the second light source whose relative position to the position of the storage area changes.

The data processing apparatus according may further includes an input portion into which identification information for specifying the analysis range is input. When the identification information is input into the input portion, the mode selection portion may select the second mode.

The input portion may be an RF tag or barcode reader.

The mode selection portion may determine whether a value acquired from the first light intensity distribution data and a value acquired from the second light intensity distribution data are greater than a predetermined value, and upon determination that the both values are greater than the predetermined value, the mode selection portion may select the first mode.

Upon determination that the value acquired from the first light intensity distribution data is greater than the predetermined value and the value acquired from the second light intensity distribution data is not greater than the predetermined value, the mode selection portion may select the second mode.

The predetermined value may be a value of light intensity or a value of time or distance.

The first light intensity distribution data and the second light intensity distribution data may be data acquired when the detection target is not stored in the storage area.

The mode selection portion may determine whether a value acquired from the first light intensity distribution data and a value acquired from the second light intensity distribution data are less than a predetermined value, and upon determination that the both values are less than the predetermined value, the mode selection portion may select the first mode.

Upon determination that the value acquired from the first light intensity distribution data is less than the predetermined value and the value acquired from the second light intensity distribution data is greater than or equal to the predetermined value, the mode selection portion may select the second mode.

In the second mode, the data determination portion may specify the analysis range of the second light intensity distribution data on the basis of correction information on a position of the analysis range of the second light intensity distribution data, with respect to a position of the analysis range of the first light intensity distribution data.

The correction information may be a constant value determined in advance with regard to the first light source and the second light source. The constant value may be based on a distance between the first light source and the second light source and on a speed at which the relative positions change. The constant value may be based on a difference between a time when the first light source passes through a predetermined point and a time when the second light source passes through the predetermined point.

According to the present technology, the reis provided an optical detection system including: a first light source and a second light source that emit light to a detection area; and a data processing apparatus including a data determination portion that specifies, in each of first light intensity distribution data and second light intensity distribution data, an analysis range corresponding to a storage area for storing a detection target, the first light intensity distribution data being acquired on the basis of the light emitted from the first light source to the detection area, the second light intensity distribution data being acquired on the basis of the light emitted from the second light source to the detection area, and a mode selection portion that selects an operation mode of the data determination portion. The mode selection portion selects one of a first mode in which the data determination portion specifies the analysis range in each of the first light intensity distribution data and the second light intensity distribution data, and a second mode in which the data determination portion specifies the analysis range in the second light intensity distribution data on the basis of information on the analysis range of the first light intensity distribution data.

The first light source and the second light source may be comprised in one unit and may be configured to be movable together.

The first light source and the second light source may be each provided to a plurality of units and the units may be configured to be separately movable.

According to the present technology, there is provide a data processing method including: specifying, by a data determination portion, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area. A mode selection portion selects one of a first mode in which the data determination portion specifies the analysis range in each of the first light intensity distribution data and the second light intensity distribution data, and a second mode in which the data determination portion specifies the analysis range in the second light intensity distribution data on the basis of information on the analysis range of the first light intensity distribution data.

According to the embodiment of the present technology, there is provided a data processing program causing a computer to perform: a function of specifying, by a data determination portion, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area; and a function of selecting, by a mode selection portion, one of a first mode in which the data determination portion specifies the analysis range in each of the first light intensity distribution data and the second light intensity distribution data, and a second mode in which the data determination portion specifies the analysis range in the second light intensity distribution data on the basis of information on the analysis range of the first light intensity distribution data.

Advantageous Effects of Invention

According to the present technology, there is provided, inter alia, a data processing apparatus that can accurately specify, in a series of light intensity data, a range corresponding to an area storing a sample.

BRIEF DESCRIPTION OF DRAWINGS

FIG. 8A and FIG. 8B are diagrams illustrating predetermined values $\alpha 1$ and $\alpha 2$ of a data processing method according to the present technology.

FIG. 9A and FIG. 9B are diagrams illustrating one example of light intensity distributing data of a data processing method according to the present technology.

FIG. 11A and FIG. 11B are diagrams for explaining how to specify an analysis range in the first mode.

FIG. 15 is a diagram illustrating correction information for an optical detection system according the second embodiment.

DESCRIPTION OF EMBODIMENTS

Hereinafter, preferred embodiments for carrying out the present technology are explained. The below-described embodiments are typical embodiments of the present technology. The scope of the present technology should not be thereby narrowed.

Figure 1:
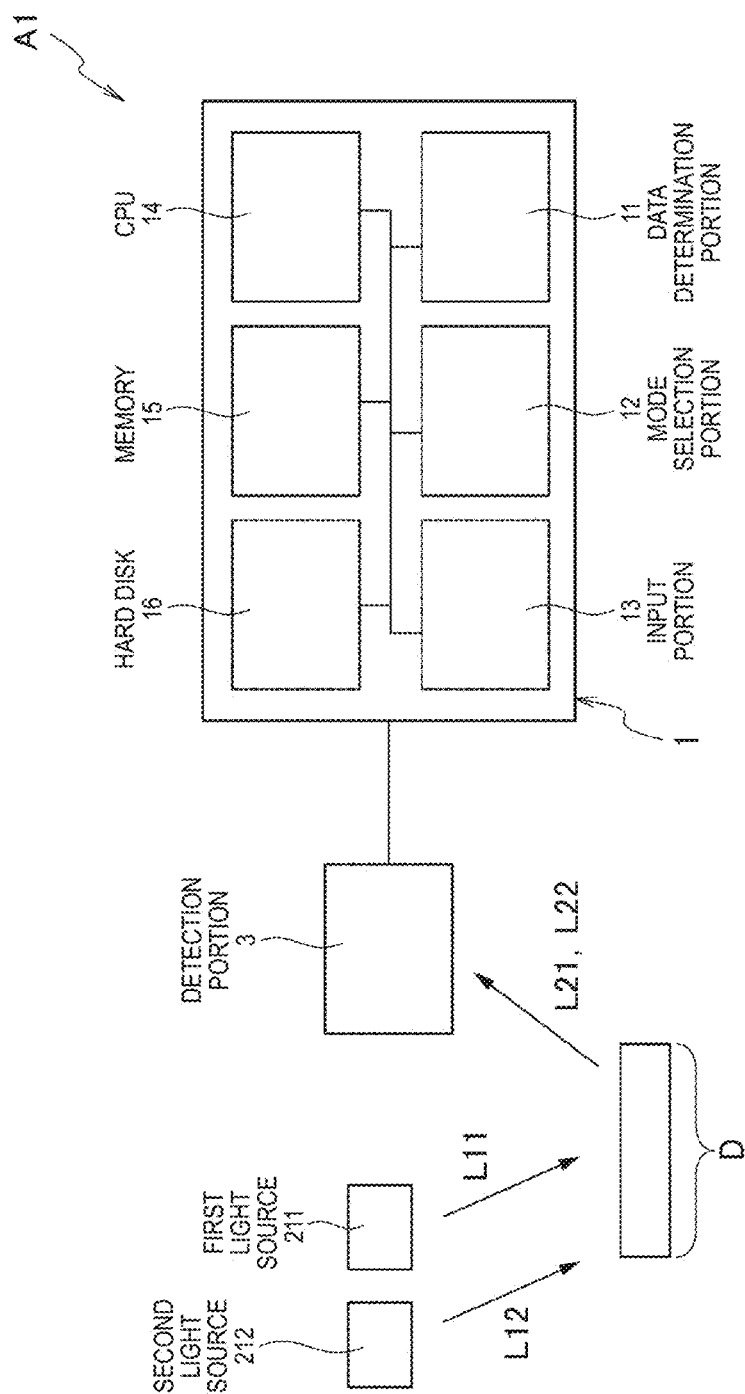
FIG. 1 is a block diagram of an optical detection system according to a first embodiment of the present technology.

(1) Optical Detection System According to First Embodiment of the Present Technology An optical detection system according to a first embodiment of the present technology is hereinbelow explained in reference to FIGS. 1 to 4. FIG. 1 is a block diagram of an optical detection system A1 according to the first embodiment of the present technology. The optical detection system A1 is a system for optically detecting a detection target. In the optical detection system A1, a detection target can be any article that can be optically detected by irradiating light emitted from below-mentioned light sources (a first optical source 211 and a second light source 212). Example types of detection targets include: nucleic acids, such as DNA and RNA; biological microparticles, such as peptides, proteins, and cells; and microparticles, such as particles for industrial use. With regard to nucleic acids, an amplified nucleic acid chain in a nucleic acid amplification reaction can be a detection target. When the detection targets are labeled with, inter alia, fluorescence, this label may be a detection target.

In the optical detection system A1, lights with different wavelengths are emitted from the below-mentioned light sources (the first light source and the second light source). Thus, the optical detection system A1 can be preferably used for a sample storing at least two types of detection targets. Examples of such a sample include a nucleic acid amplification reaction solution, and an example detection target is an amplified nucleic acid chain. One example detection target contained in a sample is a nucleic acid whose presence in the sample is not clear. Another example detection target is a nucleic acid whose presence in the sample has been confirmed in advance. A fluorescent labeled probe that specifically binds to each of amplified nucleic acid chains whose templates are the aforementioned nucleic acids is used, and the optical detection system A1 is used to detect the amplified nucleic acid chains. The success or failure of a nucleic acid amplification reaction can be determined by detecting amplification of the nucleic acid whose presence in the sample has been confirmed. Upon confirmation that a nucleic acid amplification reaction has been performed, it is possible to determine presence or absence of the nuclear acid whose presence in the sample is not clear.

(2) Configuration of Optical Detection System According to the First Embodiment

As illustrated in FIG. 1, the optical detection system A1 includes at least the first light source 211, the second light source 212, and a data processing apparatus 1 having a data determination portion 11 and a mode selection portion 12. Features of the optical detection system A1 are hereinbelow explained in a consecutive order:

In an explanation of the optical detection system A1 below, there are two light sources: the first light source 211 and the second light source 212. However, the optical detection system A1 may include more than two light sources.

<Light Source>

In the optical detection system A1, the first light source 211 and the second light source 212 are configured to irradiate lights (see an arrow-indicated light L11 and an arrow-indicated light L12 in FIG. 1), which are directed to detecting a detection target, onto a detection area that contains a storage area storing the detection target. The first light source 211 and the second light source 212 are light sources that irradiate lights with different wavelengths. For example, the first light source 211 and the second light source 212 can be appropriately chosen from among types of light sources used as publicly known light sources, such as laser light sources, LED light sources, and tungsten lamps.

In an explanation of the optical detection system A1 according to the first embodiment, a storage area refers to a space storing a detection target or a sample containing the detection target. For example, the storage area is an internal space of a microtube or a well provided on a microchip. The detection area is an area including the storage area corresponding to an area to which the lights L11 and L12 emitted from the first light source 211 and the second light source 212 are irradiated. The detection area corresponds to the entire area from which the lights L11 and L12 detected by a below-mentioned detection portion 3 are emitted.

Figure 2:
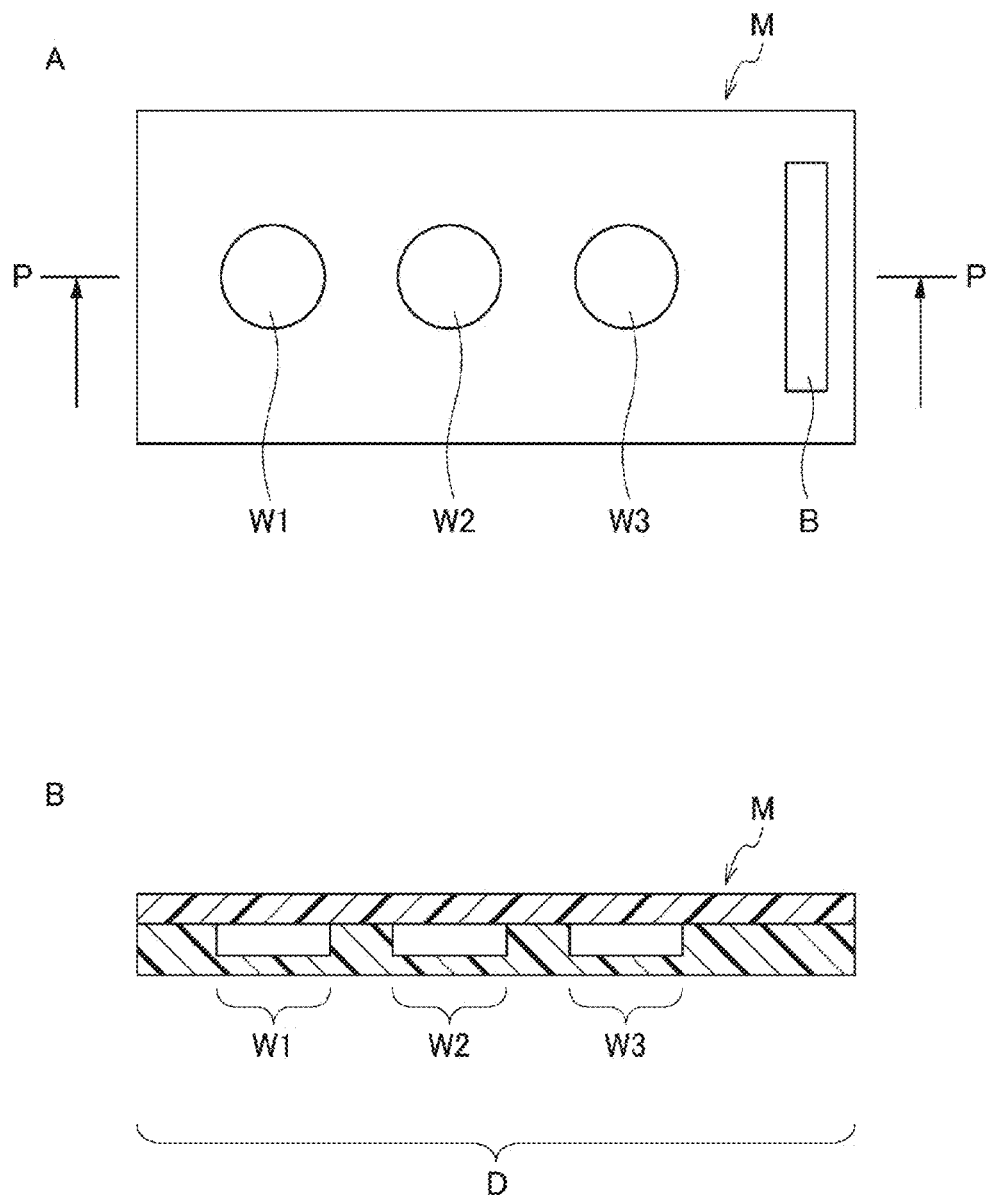
FIG. 2A and FIG. 2B are diagrams illustrating one example storage area and one example detection area of an optical detection system.

FIG. 2 illustrates one example of storage and detection areas and is a diagram illustrating a microchip M. FIG. 2A is a schematic diagram illustrating an upper surface of the microchip M, and FIG. 2B is a cross-sectional diagram along the P-P lines indicated by arrows in FIG. 2A. As illustrated in FIG. 2, when a detection target is contained in the microchip M, wells are storage areas W1, W2, and W3 that store the detection target. An area including the storage areas W1, W2, and W3 is a detection area D. In the optical detection system A1, as long as the detection area D is provided so as to include the storage areas W1, W2, and W3, there is no particular restriction with regard to the number of storage areas. In a below-mentioned data processing method using the optical detection system A1, it is preferable that the area of the detection area D is greater than the total area of the storage areas W1, W2, and W3.

Figure 3:
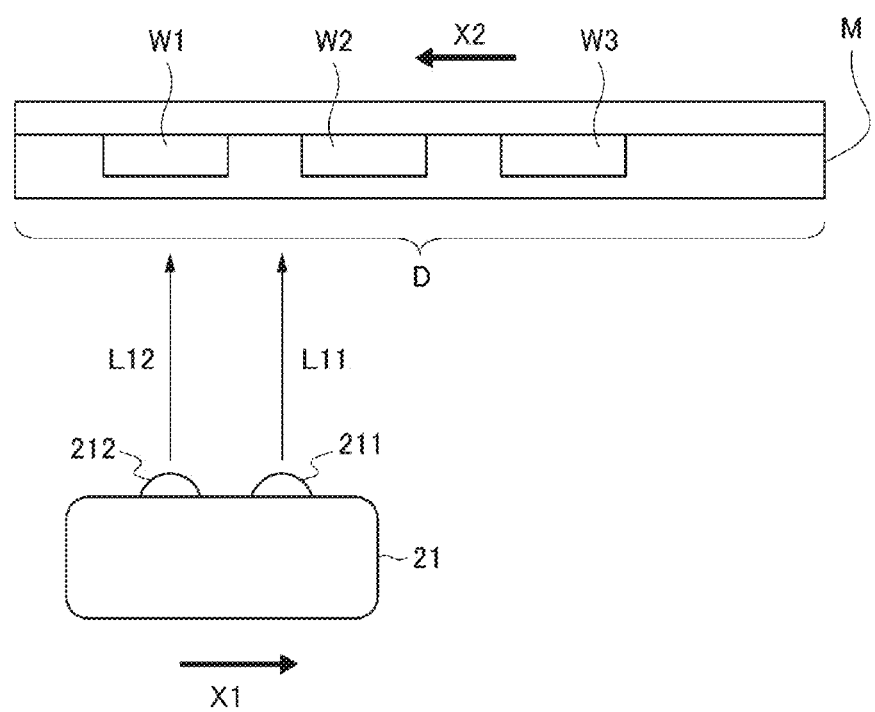
FIG. 3 is a schematic diagram illustrating an example configuration of a light source of an optical detection system according to the first embodiment.

FIG. 3 is a schematic diagram illustrating an example configuration of the first light source 211 and the second light source 212 in the optical detection system A1. The first light source 211 and the second light source 212 are provided to one unit 21. The unit 21 is configured to be movable in the direction indicated by an arrow X1.

As illustrated in FIG. 3, when the unit 21 moves in the direction indicated by the arrow X1, the first light source 211 and the second light source 212 move together. As a result, the positions of the first light source 211 and the second light source 212 change relative to the position of the detection area D.

In the optical detection system A1, the first light source 211 and the second light source 212 are provided to the one unit 21. While the positions of the first light source 211 and the second light source 212 change relative to the position of the detection area D, the light sources irradiate the light L11 and the light L12 onto the detection area D. Thereby, scanning is performed using the light L11 and the light L12, and the lights can be continuously irradiated onto a plurality of the storage areas W1, W2, and W3.

For example, by moving the microchip M instead of the unit 21 in the direction indicated by an arrow X2, the positions of the first light source 211 and the second light source 212 may be changed relative to the position of the detection area D.

Figure 4:
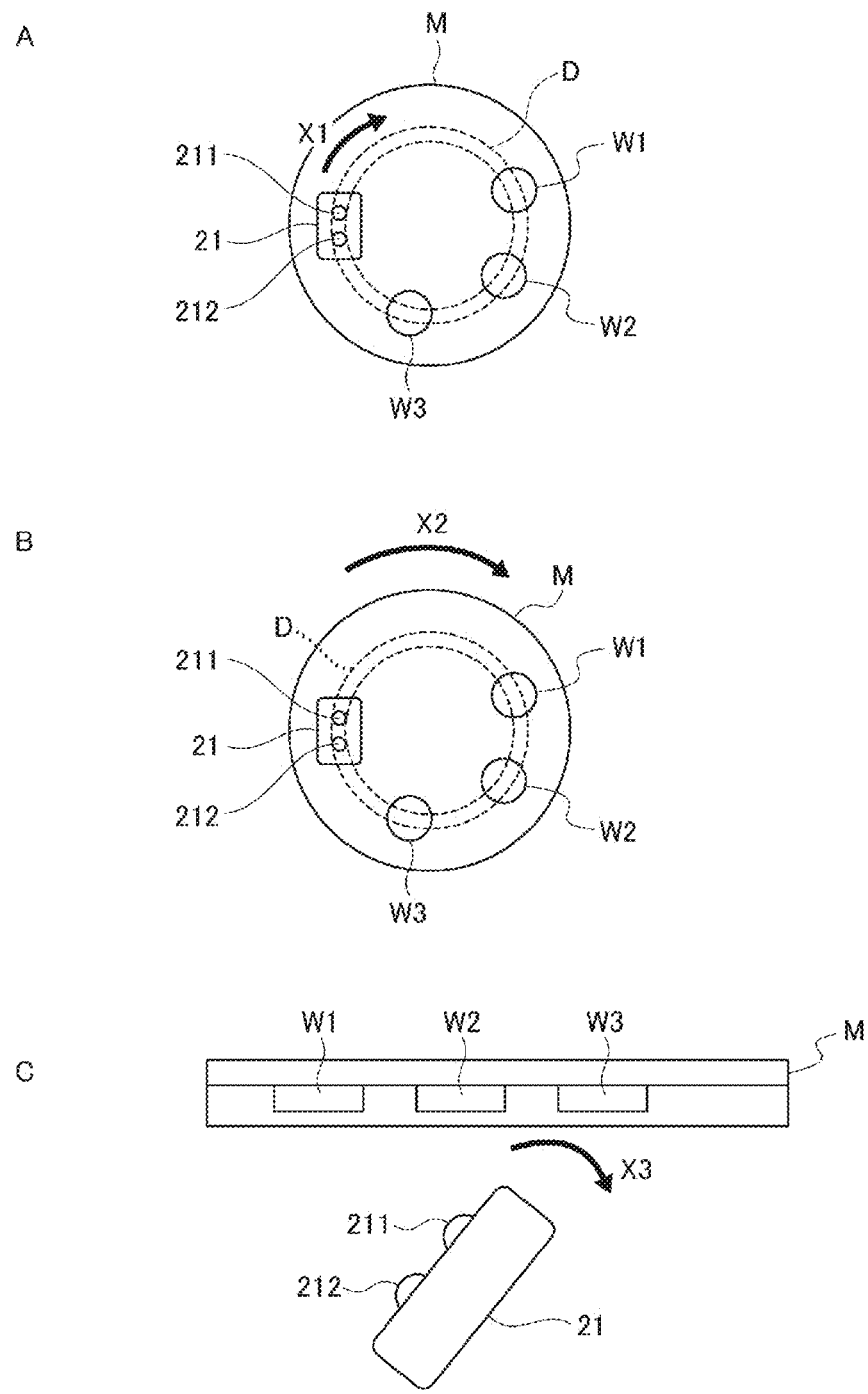
FIG. 4A to 4C are schematic diagrams illustrating example configurations of a light source of an optical detection system according to the first embodiment.

Another example configuration of the first light source 211 and the second light source 212 is illustrated in FIG. 4. As in the configuration of the first light source 211 and the second light source 212 of FIG. 3, the first light source 211 and the second light source 212 are provided in the one unit 21 in FIGS. 4A to 4C.

The top plan view of the substantially circular microchip M in FIG. 4A illustrates that the unit 21 rotates around the center of the microchip M, whereby the positions of the first light source 211 and the second light source 212 change relative to the position of the detection area D, which is surrounded by a dashed line (see an arrow X1). The top plan view of the substantially circular microchip M in FIG. 4B illustrates that the substantially circular microchip M rotates around the center of the microchip M, whereby the positions of the first light source 211 and the second light source 212 change relative to the position of the detection area D, which is surrounded by a dashed line (see an arrow X2). In the FIG. 4C, the unit 21 rotates around the center of unit 21, whereby the positions of the first light source 211 and the second light source 212 change relative to the position of the detection area D (see an arrow X3).

The optical detection system A1 having the first light source 211 and the second light source 212, both of which are mentioned above, may include an objective lens, a beam splitter, or a like feature provided to a publically known optical detection apparatus.

<Detection Portion>

The detection portion 3 is a feature for detecting lights emitted from the detection area D (arrow-indicated lights L21 and L22 in FIG. 1), the emission being induced by light irradiation from the first light source 211 and the second light source 212 to the detection area D. There is no restriction with regard to a feature of the detection portion 3 as long as the detection portion 3 can detect the lights L21 and L22 emitted from the detection area D. Example devices that can be used as the detection portion 3 include: area imaging devices, such as CCD and CMOS devices; photomultiplier tubes (PMT); and photodiodes. The detection portion 3 may be configured such that the detection portion 3 alone can detect the lights L21 and L22 alike. Also, a plurality of the detection portions 3 may be provided so that each of the plurality of the detection portions 3 detects the lights L21 and L22. As in the case of the first light source 211 and the second light source 212, the detection portion 3 may be configured in the optical detection system A1 such that the position of the detection portion 3 changes relative to the detection area D.

<Data Processing Apparatus>

As illustrated in FIG. 1, the data processing apparatus 1 includes the data determination portion 11, the mode selection portion 12, an input portion 13, a CPU 14, a memory 15, and a hard disk 16.

(Data Determination Portion)

The data determination portion 11 specifies an analysis range corresponding to a storage area storing a detection target from which intensity distribution data is acquired. Light intensity distribution data is data acquired based on respective lights emitted from the first light source 211 and the second light source 212, each of which is aforementioned, to the detection area D. Specifying of light intensity distribution data and the analysis range of the light intensity distribution data will be discussed below.

(Input Portion)

The input portion 13 reads identification information on below-described specifying of an analysis range. When this identification information is recorded in, e.g., an RF tag or a barcode B (see FIG. 2 again) placed on the microchip M, the input portion 12 may act as a reader of the barcode or RF tag. Identification information may be input by a user directly to the input portion 13, and the input portion 13 may be provided with, e.g., a keyboard in order for the user to input the identification information.

(CPU)

The CPU 14 performs overall control of features provided in the data processing apparatus 1. For example, the CPU 14 executes a program that performs overall control for the mode selection portion 12 to select the operation mode of the data determination portion 11, which will be discussed below, and for the data determination portion 11 to specify an analysis range in light intensity distribution data.

(Memory)

The memory 15 is used as a working area of the CPU 14 and temporarily stores, e.g., light intensity distribution data acquired based on light detected by the detection portion 3.

(Hard Disk)

The hard disk 16 stores, e.g., measurement data on light detected by the aforementioned detection portion 3, light intensity distribution data acquired based on detected light, and below-mentioned correction information.

To perform the aforementioned features of the data processing apparatus 1, a computer program may be developed and implemented in, e.g., a personal computer. Such a computer program may be stored in a storage medium, such as a magnetic disk, optical disk, magnetic optical disk, or flash memory or provided via a network.

Figure 5:
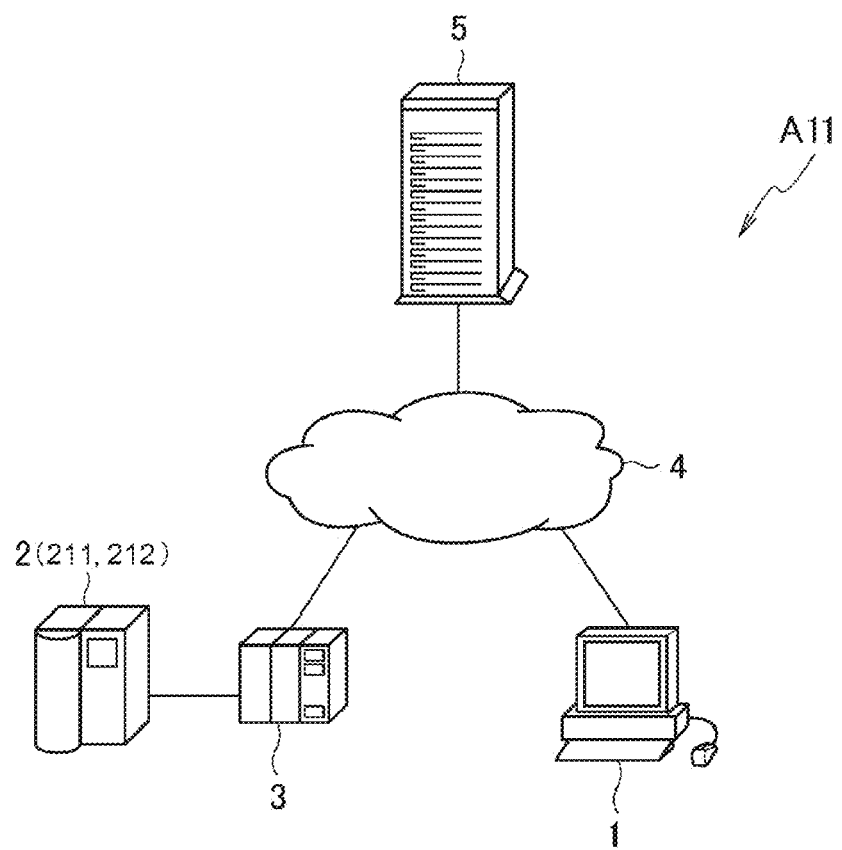
FIG. 5 is a diagram illustrating a general configuration of a modified embodiment of the first embodiment.

FIG. 5 illustrates a configuration of an optical detection system A11 according to a modified embodiment of the first embodiment. As illustrated in FIG. 1, the data processing apparatus 1 and the detector 3 may be directly connected with each other in the optical detection system according to the present technology. However, as illustrated in FIG. 5, the data processing apparatus 1 and the detector 3 may be connected via a network 4. Information stored in the aforementioned hard disk 16 may be stored in a server 5. In this case, in a below-mentioned data processing method, the data determination portion 11 and the mode selection portion 12 acquire information from the server 5 via the network 4.

(3) Data Processing Method According to the Present Technology

A data processing method using the optical detection system A1 according to the first embodiment of the present technology is hereinbelow explained. First of all, light intensity distribution data in the data processing method according to the present technology is explained below in reference to FIG. 6. For the sake of convenience, employment of the microchip M in FIG. 2 is used as an example in an explanation of the data processing method below.

<Light Intensity Distribution Data>

Figure 6:
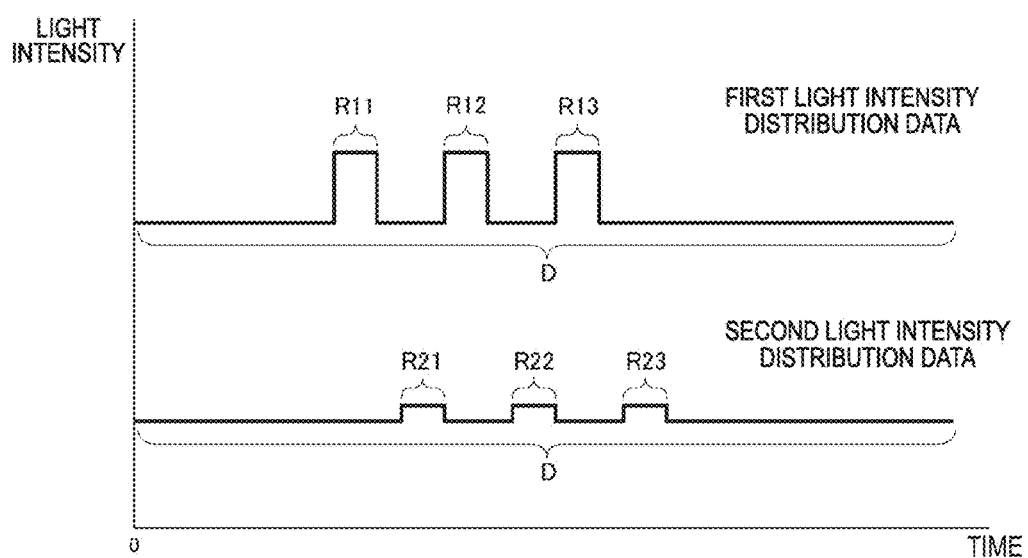
FIG. 6 is a diagram illustrating one example of light intensity distribution data of a data processing method according to the present technology.

FIG. 6 illustrates one example of light intensity distribution data stored in, e.g., the aforementioned hard disk 16. The upper half of FIG. 6 illustrates first light intensity distribution data acquired based on light emitted from the first light source 211 to the detection area D. The lower half of FIG. 6 illustrates second light intensity distribution data derived from light emitted from the second light source 212 to the detection area D.

Within the context of the data processing method according to the present technology, light intensity distribution data refers to a series of intensity data on light (light intensity data) detected by the detection portion 3 when scanning is performed using lights emitted from the aforementioned first light source 211 and the aforementioned second light source 212. Also, light intensity distribution data is data indicating the light intensity distribution in the detection area D.

In FIG. 6, the intensity of detected light is plotted on the vertical axis, and the detection time is plotted on the horizontal axis. As illustrated in FIG. 6, the light intensity distribution data may be plotted with respect to the detection time. Alternatively, light intensity distribution data may be plotted with respect to the moving distance of the unit 21 or the microchip M or with respect to the distance between one end of the detection area D to the other end.

The horizontal axes of the first and second light intensity distribution data illustrated in FIG. 6 represent time, the total of which corresponds to the detection area D. The respective light intensity distribution datum contain portions corresponding to lights emitted from the storage areas W1, W2, and W3, where a detection target is stored. Specifically, the first light intensity distribution data includes an analysis range R11 corresponding to the storage area W1, an analysis range R12 corresponding to the storage area W2, and an analysis range R13 corresponding to the storage area W3. Likewise, the second light intensity distribution data contains an analysis range R21 corresponding to the storage area W1, an analysis range R22 corresponding to the storage area W2, and an analysis range R23 corresponding to the storage area W3.

The analysis ranges R11, R12, R13, R21, R22, and R23 correspond to ranges where light intensity data derived from the detection target can be included. Specifically, the analysis ranges R11, R12, R13, R21, R22, and R23 are parts of the light intensity distribution data that are subject to analysis for, inter alia, detection and quantification of the detection target.

The first light intensity distribution data and the second light intensity distribution data, both of which are mentioned above, may be acquired when a detection target is not stored in the storage areas W1, W2, and W3. For example, the lights L11 and L12, which are emitted from the first light source 211 and the second light source 212, respectively, passed through the detection area D. In this example, the intensities of the lights L11 and L12 after having passed through the detection area D may be compared with the intensities of the lights L11 and L12 immediately after having been emitted by the first light source 211 and the second light source 212 so that the levels of attenuation of the intensities can be used as light intensities. Specifically, light intensity data based on the absorbance levels of the lights L11 and L12 may be defined as first light intensity distribution data and second light intensity distribution data, respectively.

As the aforementioned light intensity distribution data does not address light derived from the detection target, the storage areas W1, W2, and W3 are more uniform in terms of, inter alia, light intensity. In a below-mentioned data processing method, specifying of analysis ranges R11, R12, R13, R21, R22, and R23, which correspond to the plurality of the storage areas W1, W2, and W3 and are contained in the light intensity distribution data, can be readily performed under identical conditions. Light intensity distribution data acquired when the detection target is not stored in the storage areas W1, W2, and W3 can be preferably used in specifying of the analysis ranges R11, R12, R13, R21, R22, and R23 in a data processing method according to the present technology. In this case, information on the analysis ranges R11, R12, R13, R21, R22, and R23 of the first light intensity distribution data and the second light intensity distribution data can be used for specifying, in light intensity distribution data acquired after storing the detection target, analysis ranges R11, R12, R13, R21, R22, and R23 corresponding to the storage areas. When a detection target is stored in the storage areas W1, W2, and W3, there is no particular restriction with regard to the lights L11 and L12. The lights L11 and L12 may be excitation lights for the detection target or lights with wavelengths corresponding to the absorption wavelength of the detection target.

<Data Processing Method>

Figure 7:
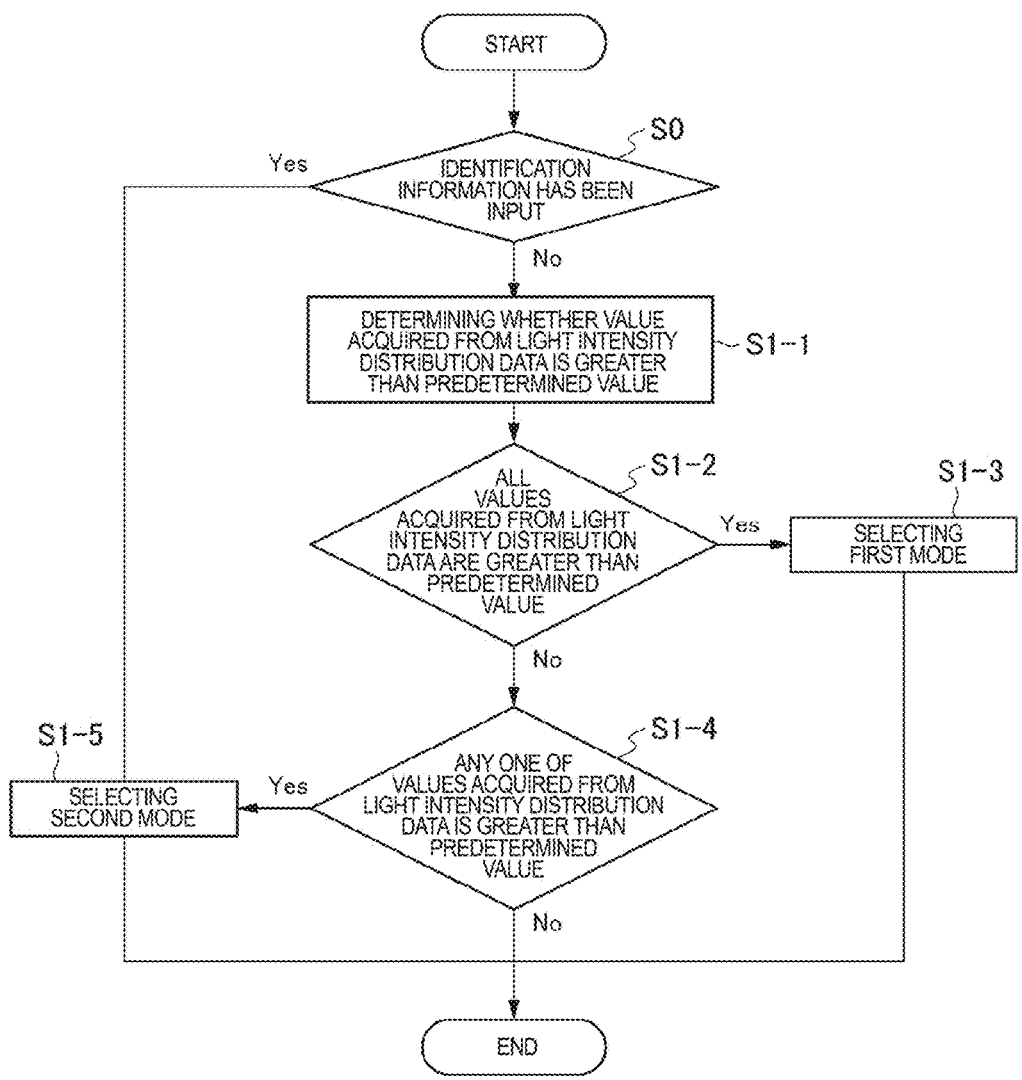
FIG. 7 is a flowchart for explaining how to select an operation mode of a data processing method according to the present technology.
Figure 10:
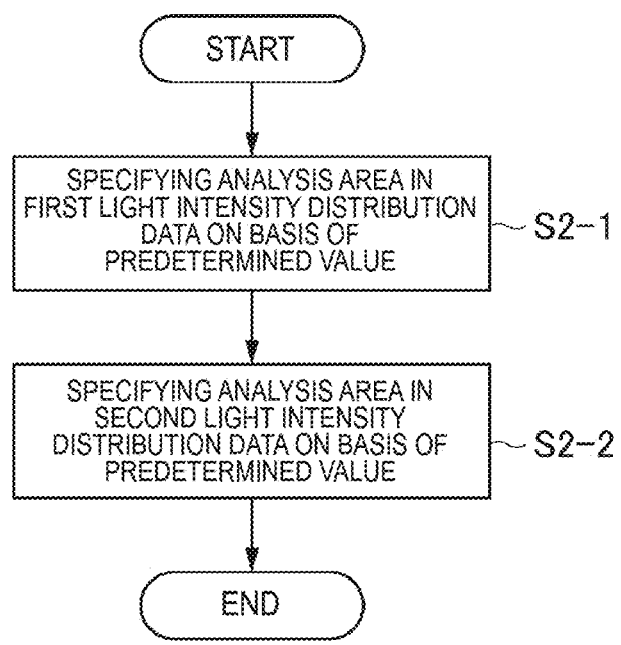
FIG. 10 is a flowchart for explaining a first mode of a data processing method according to the present technology.
Figure 12:
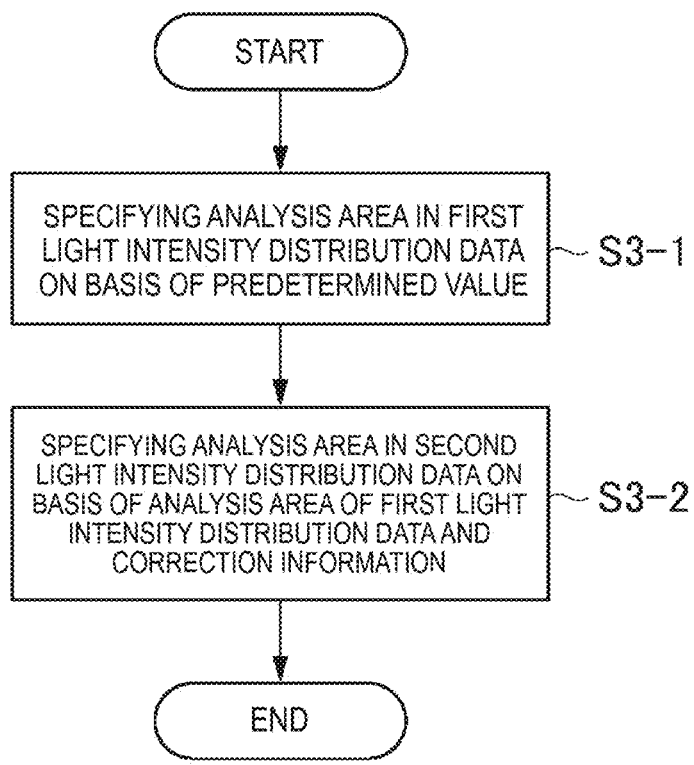
FIG. 12 is a flowchart for explaining a second mode of a data processing method according to the present technology.

The text to follow explains a data processing method according to the present technology in reference to the flowcharts (FIGS. 7, 10, and 12). The data processing method according to the present technology includes a step of selecting, by the mode selection portion 12, one of below-mentioned first and second modes as the operation mode of the data determination portion 11. Also, the data processing method according to the present technology includes a step of specifying, by the data determination portion 11, analysis ranges R11, R12, R13, R21, R22, and R23 in light intensity distribution data according to the selected operation mode.

(Selection of Operation Mode)

The flowchart illustrated in FIG. 7 shows steps of selecting the operation mode by the mode selection portion 12. When the aforementioned light detection system A1 is provided with the input portion 13, the mode selection portion 12 may confirm in step S0 whether identification information has been input. Upon confirmation that identification information for specifying an analysis range has been input into the input portion 13, the mode selection portion 12 selects the second mode (step S1-5). If identification information has not been input, the mode selection portion 12 performs step S1-1.

In step S1-1, the mode selection portion 12 determines whether a value acquired from the first light intensity distribution data and a value acquired from the second light intensity distribution data are greater than a predetermined value. The value acquired from light intensity distribution data represents, e.g., detected light intensity and detection time. The predetermined value is a value that has been set in advance and may be a value that represents, inter alia, light intensity. In addition, the predetermined value may be a value that represents time or distance.

FIG. 8 illustrates an example predetermined value in the data processing method according to the present technology. For example, a predetermined value α1 is a predetermined value representing detected light intensity (light intensity). A predetermined value α2 is a predetermined value representing the time period (from time t1 to time t2) during which the continuously detected light intensity is greater than the predetermined value α1. In this step S1-1, one predetermined value, such as the predetermined value α1, may be used as a predetermined value. Also, a plurality of predetermined values, such as the predetermined values α1 and α2, may be used in combination.

FIG. 8A illustrates an example where values acquired from light intensity distribution data are greater than the predetermined values α1 and α2. In this example, the mode selection portion 12 determines that the values acquired from the light intensity distribution data are greater than the predetermined values. FIG. 8B illustrates an example where values acquired from light intensity distribution data are not greater than the predetermined values α1 and α2. In this example, the mode selection portion 12 determines that the values acquired from the light intensity distribution data are not greater than the predetermined values.

In step S1-2, the mode selection portion 12 makes a selection according to the determination result in step S1-1. Specifically, the mode selection portion 12 selects the first mode (step S1-3) when all values acquired from first light intensity distribution data and second light intensity distribution data are greater than the predetermined value (Yes). The first mode will be explained below.

In step S1-4, the mode selection portion 12 makes a selection according to the determination result in step S1-1. Specifically, the mode selection portion 12 selects the second mode (S1-5) when the value acquired from the first light intensity distribution data is greater than the predetermined value and the value acquired from the second light intensity distribution data is not greater than the predetermined value (Yes). There is no particular restriction with regard to the first light intensity distribution data as long as the aforesaid data is acquired based on light emitted from either one of two light sources provided to the optical detection system A1. The mode selection portion 12 selects the second mode when the value acquired from one of the two types of light intensity distribution data is greater than the predetermined value.

When the values acquired from the first light intensity distribution data and the second light intensity distribution data are not greater than the predetermined value, the mode selection portion 12 does not select a mode and ends the selection step. An error is responsible for this ending. The data determination portion 11 may have the operation mode selection feature for the mode selection portion 12.

The light intensities of analysis areas R11, R12, R13, R21, R22, and R23 of first light intensity distribution data and second light intensity distribution data vary depending on, inter alia, the wavelengths of the lights L11 and L12 and whether a detection target is stored in the storage areas W1, W2, and W3. The aforementioned light intensities of the analysis areas R11, R12, R13, R21, R22, and R23 are greater than the light intensities of other areas of the light intensity distribution data in FIG. 8 and smaller than the light intensities of other areas of the light intensity distribution data in FIG. 9.

FIG. 9 illustrates one example of first light intensity distribution data (FIG. 9A) acquired based on the absorbance levels of the lights L11 and L12 and one example of second light intensity distribution data (FIG. 9B) based on the absorbance levels of the lights L11 and L12. As illustrated in FIG. 9, the light intensities of the analysis ranges R11, R12, R13, R21, R22, and R23 are lower than the light intensities of other ranges of the datum. When the mode selection portion 12 uses a predetermined value α1, which represents light intensity, with regard to the first light intensity distribution data and the second light intensity distribution data, the mode selection portion 12 determines whether respective values acquired from the first light intensity distribution data and the second light intensity distribution data are less than the predetermined value α1. The predetermined value α1 is as described above. Upon determination that all the values acquired from the first light intensity distribution data and the second light intensity distribution data are less than the predetermined value α1, the mode selection portion 12 selects the first mode. Also, upon determination that the value acquired from the first light intensity distribution data is less than the predetermined value α1 and that the value acquired from the second light intensity distribution data is greater than or equal to the predetermined value α1, the mode selection portion 12 selects the second mode.

When the optical detection system A1 is provided with more than two light sources, the mode selection portion 12 selects the second mode unless there is at least one value acquired from light intensity distribution data is greater than a predetermined value and there is at least one value acquired from the light intensity distribution data is not greater than the predetermined value.

(Specifying of Analysis Range)

In the operation mode (first or second mode) selected by the aforementioned mode selection portion 12, the data determination portion 11 specifies, in light intensity distribution data, analysis ranges R11, R12, R13, R21, R22, and R23 corresponding to the storage areas W1, W2, and W3 that store a detection target.

[First Mode]

The flowchart illustrated in FIG. 10 shows steps of the first mode of a data processing method according to the present technology. In the first mode, the data determination portion 11 specifies analysis ranges R11, R12, and R13 in first light intensity distribution data (step S2-1). Also, the data determination portion 11 specifies analysis ranges R21, R22, and R23 in second light intensity distribution data (step S-2). In the first mode, the data determination portion 11 specifies the analysis ranges R21, R22, and R23 of the second light intensity distribution data without using information on the analysis ranges R11, R12, and R13 of the first light intensity distribution data.

To specify an analysis range, the data determination portion 11 may use the aforementioned predetermined values α1 and α2. The predetermined values α1 and α2 may be equal to the values used by the mode selection portion 12 for selecting a mode (see FIG. 7). Instead of using the predetermined values α1 and α2, for example, light intensity distribution data may be plotted as illustrated in FIG. 6 so as to specify the analysis ranges based on the waveform of the light intensity distribution data.

FIG. 11A illustrates one example of step S2-1, and FIG. 11B illustrates one example of step S2-2. In reference to a predetermined value α1, the data determination portion 11 specifies, as analysis ranges R11, R12, and R13, ranges where the value of first light intensity distribution data is greater than the predetermined value α1 (time t1 to time t2, time t5 to time t6, and time t9 to time t10) (FIG. 11A). Likewise, in reference to a predetermined value α1, the data determination portion 11 determines, as the analysis ranges R21, R22, and R23, ranges where the value of second light intensity distribution data is greater than the predetermined value α1 (time t3 to time t4, time t7 to time t8, and time t11 to time t12) (FIG. 11B). As illustrated in FIG. 9, when the light intensities of the ranges determined as the analysis ranges R11, R12, R13, R21, R22, and R23 is lower than the light intensities of other ranges of the light intensity distribution data, a range whose value is less than the predetermined value α1 may be determined as an analysis range.

With regard to the predetermined value α1 representing light intensity, it is preferable to assign different values to the predetermined value α1 representing the first light intensity distribution data and the predetermined value α1 representing the second light intensity distribution data considering, inter alia, differences in the properties of the first light source 211 and the second light source 212. However, the same value may be assigned to the predetermined value α1 representing the first light intensity distribution data and the predetermined value α1 representing the second light intensity distribution data. A predetermined value α2 representing time or distance is a value corresponding to, inter alia, the sizes of the storage areas W1, W2, and W3. It is preferable to assign the same value to a predetermined value α2 representing the first light intensity distribution data and a predetermined value α2 representing the second light intensity distribution data. However, different values may be assigned to the predetermined value α2 representing the first light intensity distribution data and the predetermined value α2 representing the second light intensity distribution data.

As illustrated in FIG. 11, only one value may be assigned to the predetermined value α1 for specifying the analysis ranges R11, R12, R13, R21, R22, and R23. As in the case of the mode selection portion 12, the data determination portion 11 may use a plurality of predetermined values α1 and α2 to specify the analysis ranges R11, R12, R13, R21, R22, and R23 (see FIG. 8B).

[Second Mode]

The flowchart illustrated in FIG. 12 shows steps of the second mode according to a data processing method of the present technology. As in the case of step S2-1 of the first mode, the data determination portion 11 specifies analysis ranges R11, R12, and R13 in first light intensity distribution data in the second mode (step S3-1).

Specifying of analysis ranges R21, R22, and R23 in second light intensity distribution data is different from the first mode. Based on the analysis range of the first light intensity distribution data, the data determination portion 11 specifies the analysis ranges R21, R22, and R23 in the second light intensity distribution data (step S3-2). In the second mode, the data determination portion 11 can also specify the analysis ranges R21, R22, and R23 of the second light intensity distribution data. This specifying is made according to correction information on the positions of the analysis ranges R21, R22, and R2 of the second light intensity distribution data relative to the analysis ranges R11, R12, and R13 of the first light intensity distribution data.

It is preferable that the aforementioned correction information is a constant value determined in advance with regard to the first light source 211 and the second light source 212. Specifying of an analysis range by the data determination portion 11 is faster using a predetermined constant value as correction information than using a variable value. Example constant values include the distance between the first light source 211 and the second light source 212 as well as the speed at which the aforementioned relative positions change. When the relative position between the light source (first light source 211 or second light source 212) and the detection area D changes due to rotational movement of one of the unit 21 and the microchip M, the aforementioned distance and speed can be calculated from the angular speed and radius of the aforesaid one of the rotating bodies (see FIG. 4).

Figure 13:
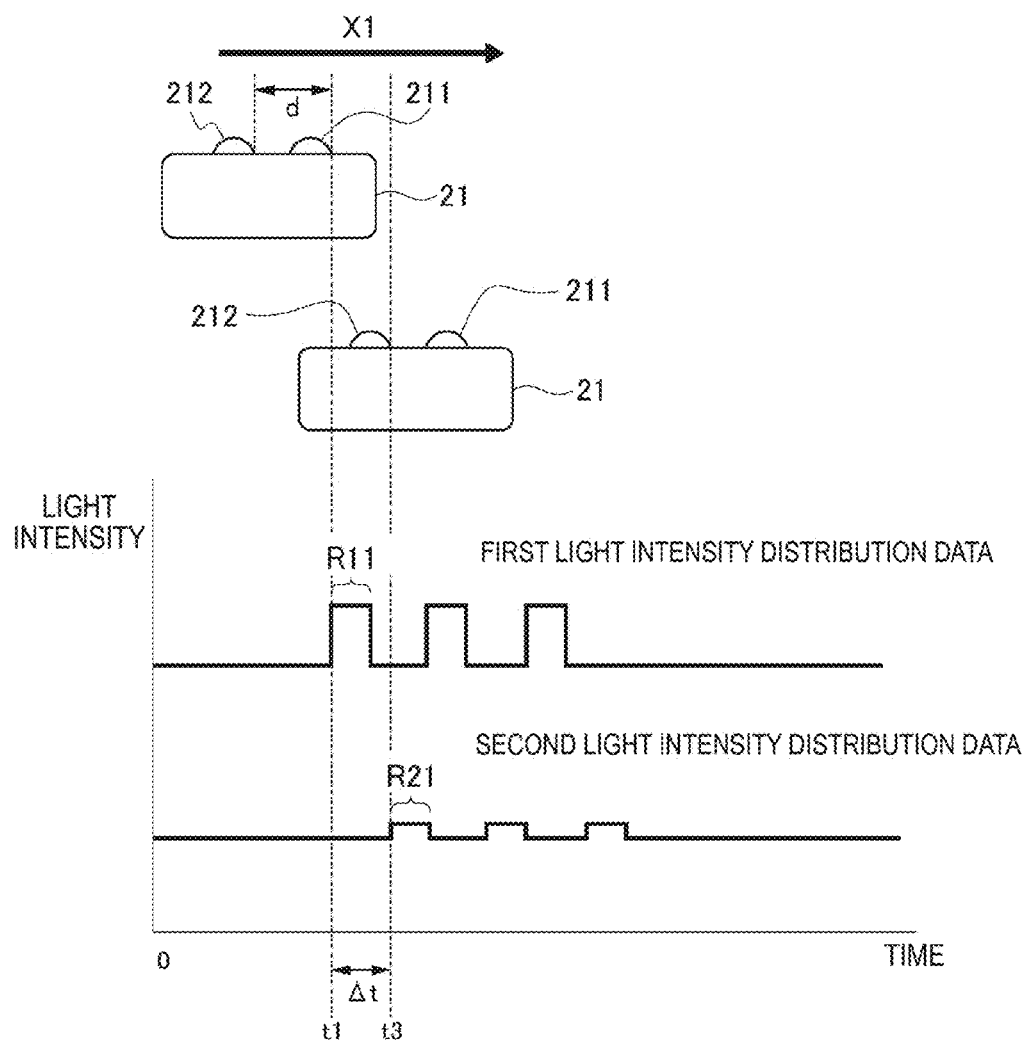
FIG. 13 is a diagram for explaining how to specify an analysis range in the second mode.

In reference to FIG. 13, the text to follow explains how a data processing method according to the present technology uses, as correction information, the distance between the first light source 211 and the second light source 212 and the time during which the relative positions change.

The unit 21 illustrated in FIG. 13 is provided with the first light source 211 and the second light source 212, and the distance between the first light source 211 and the second light source 212 is denoted by d, which is a constant value. The unit 21 moves in the direction indicated by an arrow X1, and respective lights emitted from the first light source 211 and the second light source 212 are irradiated in a consecutive order onto the storage areas W1, W2, and W3 (the storage areas W1, W2, and W3 are not shown in FIG. 13). Accordingly, a time difference (Δt) arises between the starting position of an analysis range R11 of first light intensity distribution data corresponding to the storage area W1 and the starting position of an analysis range R21 of second light intensity distribution data corresponding to the storage area W1.

The time difference (Δt) is a value that can be calculated from the distance d between the light sources and the moving speed of the unit 21. A constant value based on the distance between the first light source 211 and the second light source 212 and the speed at which the position of one of the two sources changes relative to the position of the detection area can be correction information for specifying the analysis ranges R21 as well as analysis ranges R22 and R23 in the second light intensity distribution data.

When the optical detection system A1 is provided with more than two light sources and values acquired from a plurality of light intensity distribution datum are greater than a predetermined value, it is preferable to select reference light intensity distribution data from among the plurality of light intensity distribution datum from which a value determined to be greater than the predetermined value is acquired. For example, a plurality of predetermined values representing, inter alia, light intensity and time, may be used to select, as reference data, the type of light intensity distribution data which is determined to have the greatest number of values larger than the predetermined value. The data determination portion 11 may be provided with the feature to select the aforementioned reference. Even when the second mode is selected in the aforementioned configuration of the light sources, the data determination portion 11 may specify an analysis range in each of the plurality of light intensity distribution datum, the value of which has been determined to be greater than the predetermined value, without using the aforementioned which will be discussed below.

[Second Mode—Upon Input of Identification Information]

As described above, when identification information for specifying an analysis range is input into the input portion 13, the mode selection portion 12 selects the second mode, and the data determination portion 11 specifies an analysis range by performing the steps illustrated in FIG. 12.

Identification information for specifying an analysis range may include, inter alia, information on the first light source 211. According to this information on the first light source 211, the data determination portion 11, for example, based on the value of the wavelength of light emitted by a certain light source, determines whether this light source can be the first light source 211.

The aforementioned identification information may contain, e.g., the aforementioned predetermined value and correction information. For example, in step S3-1, on the basis of a predetermined value recorded in the identification information, the data determination portion 11 can specify an analysis range in light intensity distribution data (first light intensity distribution data) acquired based on light emitted from a light source determined according to the identification information (first light source 211). In step S3-2, on the basis of information on the analysis range acquired in step S3-1 and the correction information recorded in the identification information, the data determination portion 11 can specify an analysis range of light intensity distribution data (second light intensity distribution data) acquired based on light emitted from another light source (second light source).

In a data processing method according to the present technology, an analysis range corresponding to an area storing a detection target is specified in the first light intensity distribution data and the second light intensity distribution data acquired based on lights emitted from the first light source 211 and the second light source 212, respectively. Also, when specifying an analysis range, the mode selection portion 12 selects one of two below-described modes.

In the first mode, based on a predetermined value, the data determination portion 11 specifies analysis ranges R11, R12, R13, R21, R22, and R23 in the first light intensity distribution data and the second light intensity distribution data. In the second mode, based on the information on the analysis ranges R11, R12, and R13 of the first light intensity distribution data, the analysis ranges R21, R22, and R23 are specified in the second light intensity distribution data.

Depending on the types of, inter alia, the first light source 211 and the second light source 212 used in optical detection of a detection target, for example, the optical properties of materials contained in the storage areas W1, W2, and W3 of, e.g. the microchip M can be different. It can be difficult to accurately specify an analysis range based on the aforementioned correction information due to, but not limited to the following: an error in forming, e.g., a well on the microchip M, etc.; the conditions for the optical detection system A1 to detect the detection target, such as temperature and humidity; and deviation of an optical axis caused by use. In the above situations, it is preferable to separately specify analysis ranges R11, 12, 13, 21, 22, and 23 in each of the light intensity distribution datum acquired by irradiating lights emitted from a plurality of light sources. Accordingly, the aforementioned first mode is preferable.

When the optical detection system A1 is provided with a light source unable to have a sufficient light intensity for specifying analysis ranges R21, R22, and R23, the second mode is preferable for the light intensity distribution acquired based on light emitted from the aforementioned light source.

An optimum operation mode for specifying an analysis range in light intensity distribution data differs depending on a light source or like condition. In a data processing method according to the present technology, an optimum operation mode can be selected by the mode selection portion 12. Analysis ranges R11, R12, R13, R21, R22, and R23 in light intensity distribution data can be specified more accurately.

When only the first mode can be selected and a value acquired from the second light intensity distribution data is not greater than a predetermined value, analysis ranges R21, R22, and R23 cannot be specified in second light intensity distribution data. In a data processing method according to the present technology, even when the mode selection portion 12 does not select the first mode, the data determination portion 11 can specify analysis ranges R21, R22, and R23 in the light intensity distribution data by selecting the second mode.

Figure 14:
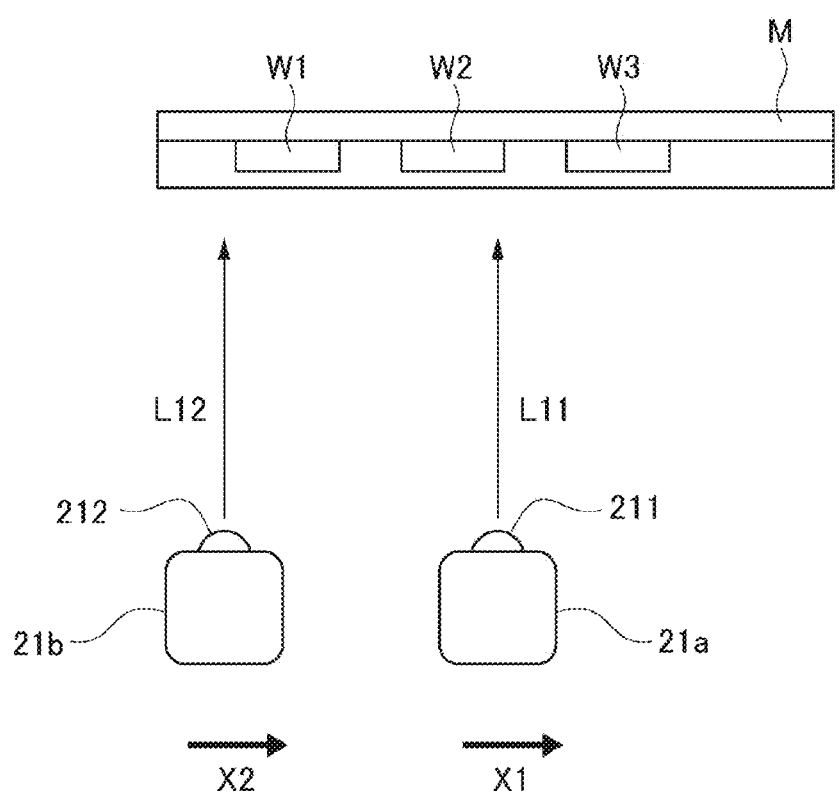
FIG. 14 is a schematic diagram illustrating an example configuration of a light source in an optical detection system according to a second embodiment of the present technology.

(4) Optical Detection System According to Second Embodiment of the Present Technology FIG. 14 is a schematic figure illustrating the first light source 211 and the second light source 212 of an optical detection system A2 according to a second embodiment of the present technology. The features of the optical detection system A2 other than the units 21a and 21b are common with the corresponding features of the first embodiment. The reference signs assigned to the common features of the first embodiment are also assigned to the common features of the second embodiment, and no explanation is given with regard to the common features.

As illustrated in FIG. 14, the first light source 211 and the second light source 212 are provided to the units 21a and 21b, respectively. In the optical detection system A2 according to the present technology, the first light source 211 and the second light source 212 may be provided to a plurality of the units 21a and 21b. Since these units 21a and 21b can move separately, the position of the first light source 211 relative to the detection area D and the position of the second light source 212 relative to the detection area D change differently (see arrows X1 and X2 in FIG. 14; and the detection area D is not shown FIG. 14).

In the optical detection system A2 that employs the units 21a and 21b, the data determination portion 11 uses correction information in the second mode. One example of the correction information is explained in reference to FIG. 15. As illustrated in FIG. 15, the units 21a and 21b move in the direction indicated by an arrow X. Correction information may be, e.g., a constant value based on the difference between the times when the first light source 211 and the second light source 212 pass through a predetermined point (reference point). The difference between the starting positions of analysis ranges R11 and R21, both of which correspond to the storage area W1, in light intensity distribution data, is based on the difference between a time t1 when the first light source 211 passes through the reference point and a time t2 when the second light source 212 passes through the reference point.

In addition, in the optical detection system A2, the data determination portion 11 may use correction information based on the difference between the starting points of movements of the plurality of the unit 21a and 21b. In the optical detection system A2, a positional sensor may be provided for the units 21a and 21b, and the data determination portion 11 may use correction information based on positional information acquired from the positional sensor.

In the optical detection system A2, it is preferable that the first light source 211 and the second light source 212 are configured so that reflection light from the detection area D, which originates from lights emitted from the aforementioned light sources (lights L11 and L12), does not enter the detection portion 3. To avoid entrance of reflection light, for example, the first light source 211 and the second light source 212 may be configured such that the timing of emitting light from the first light source 211 and the timing of emitting light from the second light source 212 are spaced apart and that the lights (lights L11 and L12) are not simultaneously emitted from the two light sources to the detection area D. Entrance of reflection light into the detection portion 3 may also be avoided by adjusting the angles and positions of the lights (lights L11 and L12) emitted from the two light sources.

In the optical detection system A2 according to the present technology, the first light source 211 and the second light source 212 are each provided to the plural units 21a and 21b. By moving the first light source 211 and the second light source 212 separately, the light L11 from the first light source 211 and the light L12 from the second light source 212 can be simultaneously irradiated onto the different storage areas W1, W2, and W3. The time taken for the optical detection system A2 to acquire light intensity distribution data can be shortened. In the optical detection system A2, to make a change or addition with regard to, e.g., the type of light source (the first light source 211 or the second light source 212), only the light source that needs to be changed, or only a necessary light source is added. Accordingly, costs for the change or addition are low. For example, the same effect can be produced in, inter alia, maintenance of the light source (first light source 211 or second light source 212). Other effects of the optical detection system A2 as the same as the corresponding effects of the optical detection system A1 according to the first embodiment.

Additionally, the present technology may also be configured as below.

(1)
A data processing apparatus including:
a data determination portion that specifies, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area; and
a mode selection portion that selects an operation mode of the data determination portion,
wherein the mode selection portion selects one of
a first mode in which the data determination portion specifies the analysis range in each of the first light intensity distribution data and the second light intensity distribution data, and
a second mode in which the data determination portion specifies the analysis range in the second light intensity distribution data on the basis of information on the analysis range of the first light intensity distribution data.

(2)
The data processing apparatus according to (1),
wherein the first light intensity distribution data and the second light intensity distribution data are acquired on the basis of light emitted from the first light source whose relative position to a position of the storage area changes, and on the basis of light emitted from the second light source whose relative position to the position of the storage area changes.

(3)
The data processing apparatus according to (1) or (2), further including:
an input portion into which identification information for specifying the analysis range is input,
wherein when the identification information is input into the input portion, the mode selection portion selects the second mode.

(4)
The data processing apparatus according to (3),
wherein the input portion is an RF tag or barcode reader.

(5)
The data processing apparatus according to any one of (1) to (4),
wherein the mode selection portion determines whether a value acquired from the first light intensity distribution data and a value acquired from the second light intensity distribution data are greater than a predetermined value, and upon determination that the both values are greater than the predetermined value, the mode selection portion selects the first mode.

(6)
The data processing apparatus according to (5),
wherein upon determination that the value acquired from the first light intensity distribution data is greater than the predetermined value and the value acquired from the second light intensity distribution data is not greater than the predetermined value, the mode selection portion selects the second mode.

(7)
The data processing apparatus according to (5) or (6),
wherein the predetermined value is a value of light intensity.

(8)
The data processing apparatus according to (5) or (6),
wherein the predetermined value is a value of time or distance.

(9)
The data processing apparatus according to (1),
wherein the first light intensity distribution data and the second light intensity distribution data are data acquired when the detection target is not stored in the storage area.

(10)
The data processing apparatus according to (9),
wherein the mode selection portion determines whether a value acquired from the first light intensity distribution data and a value acquired from the second light intensity distribution data are less than a predetermined value, and upon determination that the both values are less than the predetermined value, the mode selection portion selects the first mode.

(11)
The data processing apparatus according to (10),
wherein upon determination that the value acquired from the first light intensity distribution data is less than the predetermined value and the value acquired from the second light intensity distribution data is greater than or equal to the predetermined value, the mode selection portion selects the second mode.

(12)
The data processing apparatus according to (2),
wherein in the second mode, the data determination portion specifies the analysis range of the second light intensity distribution data on the basis of correction information on a position of the analysis range of the second light intensity distribution data, with respect to a position of the analysis range of the first light intensity distribution data.

(13)
The data processing apparatus according to (12),
wherein the correction information is a constant value determined in advance with regard to the first light source and the second light source.

(14)

The data processing apparatus according to (13), wherein the constant value is based on a distance between the first light source and the second light source and on a speed at which the relative positions change.

(15)

The data processing apparatus according to (13), wherein the constant value is based on a difference between a time when the first light source passes through a predetermined point and a time when the second light source passes through the predetermined point.

(16)

An optical detection system including:
a first light source and a second light source that emit light to a detection area; and
a data processing apparatus including
a data determination portion that specifies, in each of first light intensity distribution data and second light intensity distribution data, an analysis range corresponding to a storage area for storing a detection target, the first light intensity distribution data being acquired on the basis of the light emitted from the first light source to the detection area, the second light intensity distribution data being acquired on the basis of the light emitted from the second light source to the detection area, and
a mode selection portion that selects an operation mode of the data determination portion,
wherein the mode selection portion selects one of
a first mode in which the data determination portion specifies the analysis range in each of the first light intensity distribution data and the second light intensity distribution data, and
a second mode in which the data determination portion specifies the analysis range in the second light intensity distribution data on the basis of information on the analysis range of the first light intensity distribution data.

(17)

The optical detection system according to (16), wherein the first light source and the second light source are comprised in one unit and are configured to be movable together.

(18)

The optical detection system according to (16), wherein the first light source and the second light source are each provided to a plurality of units and the units are configured to be separately movable.

(19)

A data processing method including:
specifying, by a data determination portion, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area,
wherein a mode selection portion selects one of
a first mode in which the data determination portion specifies the analysis range in each of the first light intensity distribution data and the second light intensity distribution data, and
a second mode in which the data determination portion specifies the analysis range in the second light intensity distribution data on the basis of information on the analysis range of the first light intensity distribution data.

(20)

A data processing program causing a computer to perform:
a function of specifying, by a data determination portion, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area; and
a function of selecting, by a mode selection portion, one of
a first mode in which the data determination portion specifies the analysis range in each of the first light intensity distribution data and the second light intensity distribution data, and
a second mode in which the data determination portion specifies the analysis range in the second light intensity distribution data on the basis of information on the analysis range of the first light intensity distribution data.

REFERENCE SIGNS LIST

A1, A2, A11 optical detection system
B barcode
D detection area
M microchip
R11, R12, R13, R21, R22, R23 analysis range
W1, W2, W3 storage area
1 data processing apparatus
11 data determination portion
12 mode selection portion
13 input portion
14 CPU
15 memory
16 hard disk
2 light source
21, 21a, 21b unit
211 first light source
212 second light source
3 detection portion
4 network
5 server

The invention claimed is:

1. A data processing apparatus comprising:
a data determination portion that specifies, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area; and
a mode selection portion that selects an operation mode of the data determination portion,
wherein the mode selection portion selects one of
a first mode in which the data determination portion specifies the analysis range in each of the first light intensity distribution data and the second light intensity distribution data, and a second mode in which the data determination portion specifies the analysis range in the second light intensity distribution data on the basis of information on the analysis range of the first light intensity distribution data.

2. The data processing apparatus according to claim 1, wherein the first light intensity distribution data and the second light intensity distribution data are acquired on the basis of light emitted from the first light source whose relative position to a position of the storage area changes, and on the basis of light emitted from the second light source whose relative position to the position of the storage area changes.

3. The data processing apparatus according to claim 2, wherein in the second mode, the data determination portion specifies the analysis range of the second light intensity distribution data on the basis of correction information on a position of the analysis range of the second light intensity distribution data, with respect to a position of the analysis range of the first light intensity distribution data.

4. The data processing apparatus according to claim 3, wherein the correction information is a constant value determined in advance with regard to the first light source and the second light source.

5. The data processing apparatus according to claim 4, wherein the constant value is based on a distance between the first light source and the second light source and on a speed at which the relative positions change.

6. The data processing apparatus according to claim 4, wherein the constant value is based on a difference between a time when the first light source passes through a predetermined point and a time when the second light source passes through the predetermined point.

7. The data processing apparatus according to claim 1, further comprising:
an input portion into which identification information for specifying the analysis range is input,
wherein when the identification information is input into the input portion, the mode selection portion selects the second mode.

8. The data processing apparatus according to claim 7, wherein the input portion is an RF tag or barcode reader.

9. The data processing apparatus according to claim 1, wherein the mode selection portion determines whether a value acquired from the first light intensity distribution data and a value acquired from the second light intensity distribution data are greater than a predetermined value, and upon determination that the both values are greater than the predetermined value, the mode selection portion selects the first mode.

10. The data processing apparatus according to claim 9, wherein upon determination that the value acquired from the first light intensity distribution data is greater than the predetermined value and the value acquired from the second light intensity distribution data is not greater than the predetermined value, the mode selection portion selects the second mode.

11. The data processing apparatus according to claim 9, wherein the predetermined value is a value of light intensity.

12. The data processing apparatus according to claim 9, wherein the predetermined value is a value of time or distance.

13. The data processing apparatus according to claim 1, wherein the first light intensity distribution data and the second light intensity distribution data are data acquired when the detection target is not stored in the storage area.

14. The data processing apparatus according to claim 13, wherein the mode selection portion determines whether a value acquired from the first light intensity distribution data and a value acquired from the second light intensity distribution data are less than a predetermined value, and upon determination that the both values are less than the predetermined value, the mode selection portion selects the first mode.

15. The data processing apparatus according to claim 14, wherein upon determination that the value acquired from the first light intensity distribution data is less than the predetermined value and the value acquired from the second light intensity distribution data is greater than or equal to the predetermined value, the mode selection portion selects the second mode.

16. An optical detection system comprising:
a first light source and a second light source that emit light to a detection area; and
a data processing apparatus including
a data determination portion that specifies, in each of first light intensity distribution data and second light intensity distribution data, an analysis range corresponding to a storage area for storing a detection target, the first light intensity distribution data being acquired on the basis of the light emitted from the first light source to the detection area, the second light intensity distribution data being acquired on the basis of the light emitted from the second light source to the detection area, and
a mode selection portion that selects an operation mode of the data determination portion,
wherein the mode selection portion selects one of
a first mode in which the data determination portion specifies the analysis range in each of the first light intensity distribution data and the second light intensity distribution data, and
a second mode in which the data determination portion specifies the analysis range in the second light intensity distribution data on the basis of information on the analysis range of the first light intensity distribution data.

17. The optical detection system according to claim 16, wherein the first light source and the second light source are comprised in one unit and are configured to be movable together.

18. The optical detection system according to claim 16, wherein the first light source and the second light source are each provided to a plurality of units and the units are configured to be separately movable.

19. A data processing method comprising:
specifying, by a data determination portion, in each of first light intensity distribution data and second light intensity distribution data, an analysis range corresponding to a storage area for storing a detection target, the first light intensity distribution data being acquired on the basis of light emitted from a first light source to a detection area, the second light intensity distribution data being acquired on the basis of light emitted from a second light source to the detection area, wherein a mode selection portion selects one of
- a first mode in which the data determination portion specifies the analysis range in each of the first light intensity distribution data and the second light intensity distribution data, and
- a second mode in which the data determination portion specifies the analysis range in the second light intensity distribution data on the basis of information on the analysis range of the first light intensity distribution data.

* * * * *